US005973229A

United States Patent [19]
Walton et al.

[11] Patent Number: 5,973,229
[45] Date of Patent: Oct. 26, 1999

[54] GENE ENCODING HERBICIDE SAFENER BINDING PROTEIN

[75] Inventors: Jonathan D. Walton; John S. Scott-Craig, both of East Lansing, Mich.

[73] Assignee: Board of Trustees Operating Michigan State University, East Lansing, Mich.

[21] Appl. No.: 08/845,742

[22] Filed: Apr. 25, 1997

[51] Int. Cl.$^6$ .............................. A01H 5/00; A01H 5/10; C12N 5/14; C12N 15/29

[52] U.S. Cl. ...................... 800/300; 435/320.1; 435/419; 435/468; 536/23.6; 800/278

[58] Field of Search ............................. 435/172.3, 320.1, 435/419, 69.1, 468; 536/23.6; 800/205, 250, 278, 300; 47/DIG. 1

[56] References Cited

PUBLICATIONS

An, G., "Binary Ti Plasmid Vectors," *Methods in Molecular Biology* 44:47–58 (1995).

Altschul, S.F. et al., "Basic Local Alignment Search Tool," *J. Mol. Biol.* 215:403–410 (1990).

Collazo, P., et al., "Structure and expression of the lignin O–methyltransferase gene from Zea mays L.," *Plant Molecular Biology* 20:857–867 (1992).

"Hybridization With Radioactive Probes," *Current Protocols in Molecular Biology*, John Wiley & Sons, NY (1989) 6.3.1–6.3.6.

DeVries, S. et al., "Isolation of total and polysomal RNA from plant tissues," *Plant Molecular Biology* B6:1–13 (1988).

Funatsuki, H. et al., "Fertile transgenic barley generated by direct DNA transfer to protoplasts," *Theor Appl Genet* 91:707–712 (1995).

Gowri, G. et al., "Stress Responses in Alfalfa (Medicago sativa L.)," *Plant Physiol.* 97:7–14 (1991).

Gregersen, P.L. et al., "A putative O–methyltransferase from barley is induced by funagal pathogens and UV light," *Plant Molecular Biology* 26:1797–1806 (1994).

Held, B.M. et al., "An mRNA Putatively Coding for an O–Methyltransferase Accumulates Preferentially in Maize Roots and Is Located Predominantly in the Region of the Endodermis," *Plant Physiol.* 102:1001–1008 (1993).

Kagan, R.M. et al., "Widespread Occurrance of Three Sequence Motifs in Diverse S–Adenosylmethionine–Dependent Methyltransferases Suggests a Common Structure for These Enzymes," *Arch. Biochem. Biophys.* 310(2):417–427 (1994).

Latli, B. et al., "Radiosynthesis of a Chloracetanilide Herbicide ([phenyl–4–$^3$H]Acetochlor) and a Dichloroacetamide Safener for Herbicide ([2,2–dimethyl–$^3$H]R–29148)," *Journal of Labelled Compounds nd Radiopharmaceuticals* 36(2):147–155 (1995).

Lay, M. et al., "Dichloroacetamide Antidotes Enhance Thiocarbamate Sulfoxide Detoxification by Elevating Corn Root Glutathione Content and Glutathione S–Transferase Activity," *Pesticide Biochemistry and Physiology* 6:442–456 (1976).

Maniatis, T. et al., *Molecular Cloning: A Laboratory Manual*, Cold Spring Harbor Laboratory Press, Cold Spring, NY pp. 387–389 (1982).

Newman, T.C. et al. "DST Sequences, Highly Conserved Among Plant SAUR Genes, Target Reporter Transcripts for Rapid Decay in Tobacco," *The Plant Cell* 5:701–714 (1993).

Pakusch, A. et al., "Kinetic Characterization of Caffeoyl––Coenzyme A–Specific 3–O–Methyltransferase from Elicited Parsley Cell Suspensions," *Plant Physiol.* 96:327–330 (1991).

Sambrook, J. et al., *Molecular Cloning: A Laboratory Manual*, Second Edition, vol. 2, Cold Spring Harbor Laboratory Press, Cold Spring, NY pp. 8.46–8.47 (1989).

Scott–Craig, J.S. et al., "The Cyclic Peptide Synthetase Catalyzing HC–toxin Production in the Filamentous Fungus *Cochliobolus carbonum* Is Encoded by a 15.7–Kilobase Open Reading Frame," *The Journal Of Biological Chemistry* 267(36):26044–26049 (1992).

Singh, L. et al. "The use of heparin as a simple cost–effective means of controlling background in nucleic acid hybridization procedures," *Nucl. Acids Res.* 21(14):5627–5629 (1984).

Torbert, K.A. et al., "Use of paromomycin as a selective agent for oat transformation," *Plant Cell Reports* 14:635–640 (1995).

Vignols, F. et al., "The brown midrib3 (bm3) Mutation in Maize Occurs in the Gene Encoding Caffeic Acid O–Methyltransferase," *The Plant Cell* 7:401–416 (1995).

Walton, J.D. et al., "Specific Binding of a Dichloroacetamide Herbicide Safener in Maize at a Site That Also Binds Thiocarbamate and Chloroacetanilide Herbicides," *Plants Physiol.* 109:213–219 (1995).

Zhou, H. et al., "Glyphosate–tolerant CP4 and GOX genes as a selectable marker in wheat transformation," *Plant Cell Reports* 15:159–163 (1995).

Lay, M. et al., "Dichloroacetamide Antidotes For Thiocarbamate Herbicides: Mode Of Action," *Science* 189:287–289 (1975).

Stam M, et al. "The silence of genes in transgenic plants." Ann. Bot. 79: 3–12, 1997.

(List continued on next page.)

*Primary Examiner*—Lynette F. Smith
*Assistant Examiner*—Amy J. Nelson
*Attorney, Agent, or Firm*—Harness, Dickey & Pierce, P.L.C.

[57] ABSTRACT

The cDNA encoding safener binding protein (SafBP), also referred to as SBP1, is set forth in FIG. 5 and SEQ ID No. 1. The deduced amino acid sequence is provided in FIG. 5 and SEQ ID No. 2. Methods of making and using SBP1 and SafBP to alter a plant's sensitivity to certain herbicides or a plant's responsiveness to certain safeners are also provided, as well as expression vectors, transgenic plants or other organisms transfected with said vectors and seeds from said plants.

26 Claims, 8 Drawing Sheets

OTHER PUBLICATIONS

Koziel MG, et al. "Optimizing expression of transgenes with an emphasis on post–transcriptional events." Plant Mol. Biol. 32:393–405, 1996.

Smith CJS, et al. "Antisense RNA inhibition of polygalacturonase gene expression in transgenic tomatoes." Nature 334:724–726, Aug. 25, 1988.

Gregersen PL, et al. "A putative O–methyltransferase from barley is induced by fungal pathogens and UV light." Plant Mol. Biol. 26:1797–1806, 1994.

Sasaki T, et al. GenBank Accession Number D42011, Oct. 1994.

FIGURE 1

Saf (R-29148)     metolachlor     EPTC

```
   1  CACATACACAAGCACAAGCGCACTCTAGCAATGGCTTCTGAGGTTGTCCGCCCTAGCGAC
                                      M  A  S  E  V  V  R  P  S  D    10

61  GCCGAGCTACTAAAGGCACAAGCCGACATATGGCGGCTCAGCCTCTCCTACCTCACGCCC
       A  E  L  L  K  A  Q  A  D  I  W  R  L  S  L  S  Y  L  T  P    30

121  CTGTCACTGAGGTGCGCCGTGGAGCTTGGCATCCCTACGGCGATCTACCGCCATGGCGGG
       L  S  L  R  C  A  V  E  L  G  I  P  T  A  I  Y  R  H  G  G    50

181  GCTGCCTCAGCCGCTGAGCTGGTCACGGCGCTGTCTCTCCCCTCCACTAAGCTGCCGTTC
       A  A  S  A  A  E  L  V  T  A  L  S  L  P  S  T  K  L  P  F    70

241  CTCCGCCGCCTGCTGCGGCTCCTCGCCGCGTCGGGCGTGTTCACCGTCGACAAGCAGAGC
       L  R  R  L  L  R  L  L  A  A  S  G  V  F  T  V  D  K  Q  S    90

301  TCGGAGGAGGAGCGGTACCGCATCAGCCCCGTGTCCTACCTCCTGGTGGACGGCATCCCT
       S  E  E  E  R  Y  R  I  S  P  V  S  Y  L  L  V  D  G  I  P   110

361  CACGAGGACCACATGAACCACACCGCTCTGGTGCTCACCTGCACCTCGACGCGCTACATC
       H  E  D  H  M  N  H  T  A  L  V  L  T  C  T  S  T  R  Y  I   130

421  GAGGCGGGGATAGGGCTGGCGGAGTGGTTCAAGAGGGACGTGGTCACGTCACCGTTCGAG
       E  A  G  I  G  L  A  E  W  F  K  R  D  V  V  T  S  P  F  E   150

481  GAGCTGCACGGGGCGACTCTGTTCCACGAGAGCATGGGGAGCCTCGACGCAGATTTCCAC
       E  L  H  G  A  T  L  F  H  E  S  M  G  S  L  D  A  D  F  H   170

541  GACATGGCGAGCGAGGCCTTGGACGCCCACGACAACTTCGGCATCGAGATAGCTATGCGG
       D  M  A  S  E  A  L  D  A  H  D  N  F  G  I  E  I  A  M  R   190

601  GAGTTCAGGGACTTGTTCGAGGGGATCCAGTCCATGACCTACTGCTGCGGTAACTTCGGT
       E  F  R  D  L  F  E  G  I  Q  S  M  T  Y  C  C  G  N  F  G   210

661  GATGACAAGGGTGCCAGGGCCATTGTCAAAGCCTTCCCACACATAAAATGCACTGTGCTG
       D  D  K  G  A  R  A  I  V  K  A  F  P  H  I  K  C  T  V  L   230

721  GCCCCTCCCAAGATCATTGCCACCAAACCGGCCGATGGAGCGATGATAAACTATGTCGAA
       A  P  P  K  I  I  A  T  K  P  A  D  G  A  M  I  N  Y  V  E   250

781  GGTGACATGTTCAGTTTCATTCCACCTGCTCAAACTGTCGTGCTAAAGCTTGTGCTGCAC
       G  D  M  F  S  F  I  P  P  A  Q  T  V  V  L  K  L  V  L  H   270

841  CACCTGACCGATGAGGAGTGCGTCAAGCTCCTGGCTCAATGCCGGAAGGCGATTCCTTCA
       H  L  T  D  E  E  C  V  K  L  L  A  Q  C  R  K  A  I  P  S   290

901  CGGAAGGATGGCGGGAAAGTTATAATCGGTGATATTATGATTGACCACTCTGGGCCTATG
       R  K  D  G  G  K  V  I  I  G  D  I  M  I  D  H  S  G  P  M   310

961  CTGGAAACTCACCTCCTGATGGACATCGGCATGATGACCATGACAAAAGGACGGCAGAGA
       L  E  T  H  L  L  M  D  I  G  M  M  T  M  T  K  G  R  Q  R   330

1021  GATGAAAAAGAATGGAGCGAGCTCTTCACCAAAGCAGGGTTCAGCGAATACAAGATCCTG
       D  E  K  E  W  S  E  L  F  T  K  A  G  F  S  E  Y  K  I  L   350

1081  AAGGAATTTGGAGCTCGTGTTGCCTTCGAAGTCTATCCGTGAGATTGCACCTGGACTATA
       K  E  F  G  A  R  V  A  F  E  V  Y  P  *                     363

1141  CATATATATTTACATACATATATGTATGTGTGTGGGTGCCTTGCGTGGCTTGGCGTGATG
1201  ATGTCATAAATAAAGAGGGTGGGTGTGCTTGCGGTATTCATGGATGGCCATGGATCTGAG
1261  CACATGACGTTGGATGCTTTCTTAAGGCTCTCGTGGATCTTCTATATTTGGAAGAAGCTG
1321  TAAAATAATATATCGCCATCTAGTGTTGGCGTTGGCTTGTATGTACTTTGTACCTGCTTT
1381  GTTATTTTGTGTAATATCGAGTAACCTAATGTATACTTGCTTACTACTATCACTACCG   1438
```

GENE ENCODING HERBICIDE SAFENER BINDING PROTEIN

SPONSORSHIP

Work on this invention was sponsored in part by the National Institute Of Environmental Health Sciences Grant P01 ES-00049 and the Department Of Energy Division Of Energy Biosciences Grant DEFG02-91 ER20021. The Government has certain rights in the invention.

FIELD OF THE INVENTION

The present invention relates generally to herbicide safener binding proteins and more particularly, to the gene encoding herbicide safener binding protein (SafBP), SBP1.

BACKGROUND OF THE INVENTION

Conferring resistance of plants to either their natural enemies or to those compounds used to protect them from their natural enemies has been accomplished through the techniques of genetic engineering. U.S. Pat. No. 5,306,863 teaches a method of conferring pest resistance by creating genetically transformed plants through the use of trypsin inhibitors derived from legume plants. Similarly, U.S. Pat. No. 5,317,096 describes isolated toxin genes derived from the bacterium Bacillus thuringiensis which may be used to provide transformed plants with resistance to certain insects.

With respect to herbicide resistance, U.S. Pat. No. 5,290,926 teaches the isolation and purification of the plant histidinol dehydrogenase, as well as assays to detect inhibitors of histidinol dehydrogenase (e.g., herbicides) and mutant forms of the wild-type enzyme not inhibited by inhibitors. Transgenic crop plants may thus be produced, containing the non-inhibited mutant enzyme, and these crops may be treated with histidinol dehydrogenase inhibitors to treat weeds.

U.S. Pat. No. 5,145,777 teaches conferring resistance to herbicidal glutamine synthetase inhibitors by amplification of the glutamine synthetase gene by linking it to a sequence which is capable of increasing the expression of the gene. Similarly, U.S. Pat. No. 5,276,268 describes conferring resistance to phosphinothricin, a potent glutamine synthetase inhibitor used in herbicides, through the isolation of phosphinothricin resistance genes and processes of producing plants which are transformed with such genes. U.S. Pat. No. 5,212,296 teaches isolated DNA sequences encoding herbicide-metabolizing cytochrome P450 enzymes and iron-sulfur proteins which assist these enzymes by donating electrons. Both the enzymes and helper proteins may be utilized to transform plants into having the ability to break down herbicides, thus conferring herbicide resistance.

Figure 1:
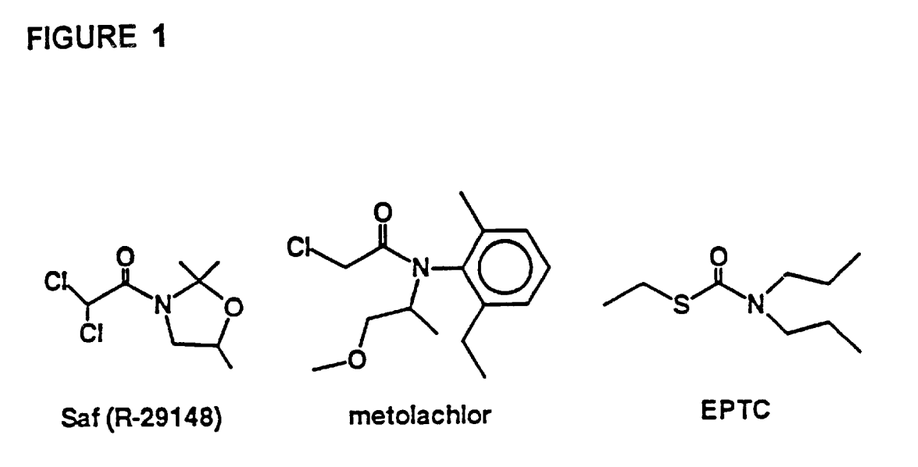
FIG. 1 provides the structures of Saf (R-29148), metolachlor (a chloroacetanilide herbicide), and S-ethyl dipropylthiocarbamate (EPTC) (a thiocarbamate herbicide)

Herbicide safeners, also known as antidodes, are used to protect plants against injury from herbicides. Widely used herbicide safeners include the dichloroacetamides such as dichlormid (R-25788), which are used in combination with thiocarbamate herbicides (e.g., EPTC) and chloroacetanilide herbicides (e.g., metolachlor), on maize and sorghum (FIG. 1). The mode of action of safeners is associated with their ability to stimulate glutathione (GSH)-mediated detoxification of herbicides (Lay, M.-M. et al., *Science* 189:287–289 (1975)), although the mechanism by which they induce this is unclear.

Etiolated maize seedlings have high-affinity binding activity for the dichloroacetamide safener R-29148 ((R,S)-3-dichloroacetyl-2,2,5-trimethyloxazolidine). Walton, J. D. and Casida, J. E., *Plant Physiol.* 109:213–219 (1995). R-29148 (Saf) is a commercially used dichloroacetamide safener and is shown in FIG. 1. The characterization of a soluble, high affinity ($K_d$=120 nM) safener binding activity (SafBA) for [$^3$H]Saf in extracts of etiolated maize seedlings has been reported. Walton, J. D. and Casida, J. E., *Plant Physiol.* 109:213–219 (1995). SafBA is sensitive to boiling and protease treatment. Although present in all tissues of the etiolated seedling, SafBA is most abundant in the coleoptile. There is good correlation between inhibition of binding and safener action among a series of Saf analogs, with dichlormid being the strongest binding antagonist of any compound tested ($IC_{50}$ 10 nM, $IC_{50}$=inhibitor concentration that reduces specific binding by 50%).

It would thus be desirable to provide the gene responsible for SafBA. It would also be desirable to isolate and purify the gene product. It would also be desirable to control SafBA in plants. It would further be desirable to control SafBA in plants by controlling the expression of the gene encoding the protein responsible for SafBA. It would also be desirable to transform plants using the gene in order to alter their sensitivity to herbicides. It would also be desirable to acquire long-term control over SafBA in plants to provide safener responsiveness in plants which are not safener responsive, and increase safener responsiveness in plants which are safener responsive. It would additionally be desirable to provide an in vitro assay to screen for new herbicides and safeners.

SUMMARY OF THE INVENTION

A safener binding protein (SafBP) responsible for safener binding activity (SafBA) is provided. The cDNA encoding SafBP is set forth in FIG. 5 and SEQ ID No. 1, and is also referred to herein as SBP1. The deduced amino acid sequence of SafBP is also provided and is set forth in FIG. 5 and SEQ ID No. 2. The protein has a mass of approximately 39 kd by sodium dodecyl sulfate polyacrylamide gel electrophoresis (SDS-PAGE) and an isoelectric point of approximately 5.5. An antiserum raised against purified SafBP binds to a 39 kd protein in etiolated maize and sorghum but not in etiolated wheat, oat, barley, tobacco, or Arabidopsis. Consistent with earlier binding studies, SafBP is most abundant in the coleoptile and scarcest in leaves.

In addition to safeners, SafBP binds active chloroacetanilide herbicides, exemplified by metolachlor, alachlor, acetochlor, and propachlor, and thiocarbamate herbicides, including but not restricted to EPTC, cycloate, butylate, and triallate. For example, the chloroacetanilide metolachlor ($IC_{50}$ 40 nM) and the thiocarbamate EPTC ($IC_{50}$ 110 nM) are both strong competitive inhibitors of [$^3$H]Saf binding. On the basis of its biochemical properties, it is likely that SafBP represents the initial site of action of dichloroacetamide safeners, and possibly also the initial site of the chloroacetanilide and thiocarbamate herbicides.

Methods of making and using the cDNA encoding SafBP and SafBP are also provided. For example, SBP1 may be used to alter a plant's sensitivity to certain herbicides and increase a plant's responsiveness to certain safeners. Expression vectors containing the cDNA, transgenic plants and other organisms, e.g., *E. coli*, transfected with said vectors as well as seeds from said plants, are also provided by the present invention. In addition, an in vitro binding assay is provided which may be used to screen for herbicides and safeners.

Additional objects, advantages, and features of the present invention will become apparent from the following description, in conjunction with the accompanying drawings.

BRIEF DESCRIPTION OF THE DRAWINGS

The various advantages of the present invention will become apparent to one skilled in the art by reading the following specification and by referencing the following drawings in which:

FIG. 5 is the nucleotide sequence of the CDNA (SEQ ID No. 1) encoding SafBP and its deduced amino acid sequence (SEQ ID No. 2);

DETAILED DESCRIPTION OF THE PREFERRED EMBODIMENTS

The cDNA sequence encoding SafBP, also referred to as SBP1, is set forth in FIG. 5 and SEQ ID No. 1. The deduced amino acid sequence is provided in FIG. 5 and SEQ ID No. 2. The protein has a mass of approximately 39 kd by SDS-PAGE and an isoelectric point of approximately 5.5. By sequence comparison, SBP1 is predicted to encode a phenolic O-methyltransferase.

The sequences of the present invention may be used to alter a plant's sensitivity to certain herbicides and increase a plant's responsiveness to certain safeners. The method of imparting herbicide tolerance to a plant includes the steps of introducing an expression vector comprising a cDNA encoding SafBP or a functional mutant thereof, operably linked to a promoter functional in a plant cell into the cells of plant tissue and expressing the encoded protein in an amount effective to render the plant tissue substantially tolerant to the herbicide. The level of expression can be increased by either combining the cDNA with a promoter that provides for a high level of expression, or by introducing multiple copies into the cell so that the multiple copies are integrated into the genome of transformed plant cells. Once transformed cells exhibiting herbicide tolerance are obtained, transgenic plants and seeds can then be regenerated therefrom, and evaluated for stability of the inheritance of the herbicide tolerance and/or safener responsiveness trait.

The SBP1 nucleotide sequence may thus be fused to a gene or fragment thereof, which allows it to be expressed in a plant cell. SBP1 in combination with the gene or gene fragment, is referred to as an "expression vector" herein. It will be appreciated that the expression vectors of the present invention may contain any regulatory elements necessary and known to those skilled in the art for expression of SBP1. For example, such vectors may contain, but are not limited to, sequences such as promoters, operators and regulators, which are necessary for and/or may enhance the expression of the SafBP.

The nucleic acid sequence of the present invention may thus be used to genetically engineer plants to enhance their responsiveness to safeners and/or to alter their sensitivity to herbicides. For example, since members of the cereal family such as oats, wheat and barley do not have either SafBP or SafBA, they and other crops which lack the gene encoding SafBP could be transformed with SBP1 and would thus become responsive to safeners. This would allow the use of herbicides such as thiocarbamates and chloroacetanilides against which the dichloracetamide safeners protect, on these crops. Other plants, such as dicot crops, might also be agronomically improved by transformation with SBP1. Furthermore, because SafBP also binds herbicides themselves, transgenic plants expressing SafBP may become resistant to the herbicides as a result of the herbicides being removed from metabolism within the cell for example, by binding.

The invention also provides for a method of producing SafBP in a host cell. The method includes the steps of introducing an expression vector comprising a cDNA encoding a plant SafBP or functional mutant thereof into a host cell and expressing the cDNA in an amount sufficient to permit purification of the plant SafBP. A vector may include a promoter that is functional in either a eukaryotic or a prokaryotic cell. Preferably, the vector is introduced into a prokaryotic cell, such as *E. coli*, that is routinely used for production of recombinantly produced proteins. In addition, the availability of large amounts of purified recombinant protein can permit the rapid screening of new compounds to identify new herbicides and safeners. It is further contemplated that SafBP may be manufactured using standard synthetic methods.

It will also be appreciated that purified protein from a plant such as maize is also contemplated within the present invention, and can also be used to screen for new compounds. For example, an in vitro binding assay is provided wherein the safener or herbicide of interest is incubated with a radiolabeled safener, along with extracts of a host expressing SBP1, e.g., *E. coli*, yeast, tobacco, *Bacillus subtilis*, etc. Extracts of *E. coli* cells expressing SBP1 have strong R-29148 binding that, like binding to the native maize protein, is competitively inhibited by the safener dichlormid and the herbicides EPTC, alachlor, and metolachlor. Thus, in a preferred embodiment, the host is *E. coli*, and the radiolabeled safener is [$^3$H]R-29148. The extracts are then filtered and the radioactivity retained on the filters determined by standard techniques. The in vitro binding assay of the present invention provides for screening of new compounds more rapidly than known whole plant assays.

As referred to herein, the term "cDNA" is meant a nucleic acid, either naturally occurring or synthetic, which encodes a protein product. The term "nucleic acid" is intended to mean natural and/or synthetic linear, circular and sequential arrays of nucleotides and nucleosides, e.g., cDNA, genomic DNA (gDNA), mRNA, and RNA, oligonucleotides, oligonucleosides, and derivatives thereof. The term "encoding" is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell. As used herein, "polypeptide" refers to an amino acid sequence which comprises both full-length protein and fragments thereof.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID No. 1 or portion thereof), with a second target nucleic acid sequence. "High stringency conditions" for the annealing process may involve, for example, high temperature and/or lower salt content, which disfavor hydrogen bonding contacts among mismatched base pairs. "Low stringency conditions" would involve lower temperature, and/or higher salt concentration than that of high stringency conditions. Such conditions allow for two DNA strands to anneal if substantial, as is the case among DNA strands that code for the same protein but differ in sequence due to the degeneracy of the genetic code. Appropriate stringency conditions which promote DNA hybridization, for example, 6× SSC at about 45° C., followed by a wash of 2× SSC at 50° C., are known to those skilled in the art or can be found in *Current Protocols in Molecular Biology*, John Wiley & Sons, N.Y. (1989), 6.31–6.3.6. For example, the salt concentration in the wash step can be selected from a low stringency of about 2× SSC at 50° C., to a high stringency of about 0.2× SSC at 50° C. In addition, the temperature in the wash step can be increased from low stringency at room temperature, about 22° C., to high stringency conditions, at about 65° C. Other stringency parameters are described in Maniatis, T., et al., *Molecular Cloning: A Laboratory Manual*, Cold Spring Harbor Laboratory Press, Cold Spring N.Y., (1982), at pp. 387–389; see also Sambrook J. et al., *Molecular Cloning: A Laboratory Manual*, Second Edition, Volume 2, Cold Spring Harbor Laboratory Press, Cold Spring, N.Y. at pp. 8.46–8.47 (1989).

The foregoing and other aspects of the invention may be better understood in connection with the following examples, which are presented for purposes of illustration and not by way of limitation.

SPECIFIC EXAMPLE 1

Materials and Methods

Plant Material. Genotypes and sources of plant materials are described in Walton, J. D. and Casida, J. E., *Plant Physiol.* 109:213–219 (1995). SafBP and SafBP cDNAs were isolated from maize (*Zea mays L.*) inbred B73. The *Arabidopsis thaliana* ecotype was Columbia and the tobacco cultivar was SR-1. All plants were grown in the dark on wet paper towels for 4 to 7 d.

Binding Assay. Racemic R-29148 (Saf) and [$^3$H]Saf (specific activity 15 Ci/mmol) were prepared according to Latli, B. et al., *J. Labelled Cmpd Radiopharmn.* 36:147–155 (1995). The sources of other chemicals are given in Walton, J. D. and Casida, J. E., *Plant Physiol.* 109:213–219 (1995). [$^3$H]Saf binding was measured by incubating extracts with ca. 400,000 cpm of [$^3$H]Saf in 50 mM Tris-HCl, pH 8, in a total volume of 1 mL for 60 min at 22° C. The extracts were then filtered through GF/A (Whatman) glass fiber filters that had been soaked in 0.3% polyethylenimine, the filters rinsed with water, and radioactivity retained on the filters measured by scintillation counting. Walton, J. D. and Casida, J. E., *Plant Physiol.* 109:213–219 (1995).

Purification of SafBP. Maize coleoptiles (typically 5 to 10 gm FW) were ground in 50 mM Tris-HCl, pH 8, plus 0.4 M sucrose. After filtering through cheesecloth, ammonium sulfate was added to the extracts to 50% saturation (29.5 gm/100 mL) and centrifuged (10,000 g, 15 min) after 30 min stirring at 4° C. Ammonium sulfate was added to the supernatant to a final concentration of 70% saturation (an additional 12.7 gm/100 mL) and after stirring and centrifugation the pellet was redissolved in chromatofocusing start buffer (25 mM piperazine-HCl, pH 6.3) and desalted on a PD-10 gel filtration column (Pharmacia).

The protein extract was fractionated by chromatofocusing on a Mono P HR5/20 column (Pharmacia). Elution buffer was 10% (v/v) Polybuffer 74 (Pharmacia) adjusted to pH 4.6 with HCl. Fractions (each 1 mL) with binding activity were pooled and adjusted to 0.1 M $KH_2PO_4/K_2HPO_4$, pH 7, and 1.7 M ammonium sulfate. This preparation was then fractionated by hydrophobic interaction chromatography on a TSK-Phenyl-5-PW (Bio-Rad) HPLC column. Buffer A was 0.1 M $KH2PO_4/K_2HPO_4$, pH 7, plus 1.7 M ammonium sulfate, and buffer B was water. The gradient was 100% A to 100% B in 30 min at a flow rate of 1 mL/min. Fractions (each 1 mL) with binding activity were pooled, desalted on a PD-10 column and fractionated by anion exchange chromatography on a TSK-DEAE-5-PW HPLC column. Buffer A was 25 mM Tris-HCl, pH 8, and buffer B was 25 mM Tris-HCl plus 0.8 M KCl. The gradient was 100% A to 100% B in 30 min at a flow rate of 1 mL/min. One-mL fractions were collected. At this point, SafBP was homogeneous as determined by SDS-PAGE (12% [v/v] acrylamide). Scott-Craig, J. S. et al., *J. Biol. Chem.* 67:26044–26049 (1992).

Purified SafBP was blocked at the N-terminus. Internal peptides were generated by digestion with trypsin or endoproteinase Asp-N (Boehringer-Mannheim), fractionated by microbore reverse-phase HPLC, and sequenced by automated Edman degradation.

Antibody Preparation. Purified SafBP (50 $\mu$g) was homogenized in Titermax adjuvant (CytRx, Norcross, Ga.) and injected sub-cutaneously into New Zealand white rabbits. Rabbits were bled after 42 d and 56 d without any boost. The crude antiserum could detect SafBP on immunoblots at a 1:16,000 dilution and was used routinely at 1:5000 dilution. SDS-PAGE gels were blotted to 0.2$\mu$pore size nitrocellulose (Schleicher and Schuell). Bound anti-SafBP antibody was detected using goat anti-rabbit IgG conjugated to alkaline phosphatase (Kirkegaard and Perry Laboratories, Gaithersburg, Md.). Scott-Craig, J. S. et al., *J. Biol. Chem.* 67:26044–26049 (1992). Prestained molecular mass standards were from Gibco-BRL.

Cloning of an SBP1 cDNA by PCR. Routine nucleic acid manipulations were carried out as described in Sambrook et al. (Sambrook, J., et al., *Molecular Cloning: A Laboratory Manual*, 2nd ed., Cold Spring Harbor Laboratory, Cold Spring Harbor, N.Y. (1989)) unless otherwise specified. The cDNA library was made from polyA$^+$-RNA extracted from 12 day-old etiolated maize seedlings of inbred B73 in vector λZipLox (Gibco-BRL, Bethesda, Md.).

Polymerase chain reaction (PCR) was done with DNA extracted from the cDNA library as template. PCR reactions were carried out in 100-$\mu$L final volumes using 0.25 U of Taq polymerase (Promega), 20 mM Tris, pH 8.9, 50 mM KCl, 0.01% Triton X-100, 1 mM DTT, 1.5 mM $MgCl_2$, 300 $\mu$M deoxynucleotide triphosphates, 1 $\mu$M of each primer, and 5 $\mu$g of cDNA library template for 45 cycles (one cycle is 94° C. for 1 min, 50° C. for 2 min, and 72° C. for 3 min). Table I below provides the sequences of peptides obtained from purified SafBP. Peptide Nos. 1 and 7 were obtained with trypsin and the others with endoproteinase Asp-N. Parentheses indicate uncertain identification and X indicates unknown. Amino acids in lowercase indicate differences between the peptides and the deduced amino acid sequence of SBP1. Peptide No. 5 was obtained twice from two digestions. Three pairs of degenerate primers based on the amino acid sequences of Peptide Nos. 5, 6, and 8 in Table I were synthesized in both orientations and tried in all combinations. A portion of the cDNA encoding SafBP was successfully amplified using primer 235 (5'-GAYAAYTTYGGNATHGA (SEQ ID NO:3), based on the amino acid sequence DNFGIE (SEQ ID NO:4) in Peptide No. 5; see Table I) and primer 240 (5'-GCNCCRAAYTCYTTNA (SEQ ID NO:5), based on LKEFGA (SEQ ID NO:6) in Peptide No. 8; see Table I). Y is C or T, N is any nucleotide, R is A or G, and H is A, T, or C. The PCR products were separated by gel electrophoresis (0.7% agarose), blotted onto Nytran membrane (Schleicher and Schuell), and amplification of the correct DNA sequence was tested by hybridization at 46° C. with radiolabeled primer 237 (5'-GARTAYAARATHCTNAA (SEQ ID NO: 7), based on the amino acid sequence EYKILK (SEQ ID NO:8) in Peptide No. 8; see Table I). For hybridization the primer (50 pmol) was labelled in a 25 $\mu$L reaction at 37° C. for 15 min using 66 pmol of [$\gamma^{32}$P]ATP (Dupont), 10 U T4 polynucleotide kinase (New England Biolabs) and buffer supplied by the manufacturer. Hybridization was at 46° C. The PCR product was cloned into the EcoRV site in pBluescript (Stratagene) and again confirmed by hybridization with probe 237 and by sequencing. The PCR product was used as a probe to isolate cDNAs from the library and the entire sequence of both strands of one was determined by automated fluorescent sequencing at the MSU-DOE-PRL Plant Biochemistry Facility. Sequences were analyzed by BLAST (Altschul, S. F. et al., *J. Mol. Biol.* 215:403–410 (1990)), DNASIS (Hitachi, San Bruno, Calif.), and PILEUP (Program Manual for the Wisconsin Package, Genetics Computer Group, Madison, Wis. (1994)).

(Gibco-BRL). Equal loading of lanes was confirmed by staining of the rRNA bands with ethidium bromide.

Results

Figure 2A:
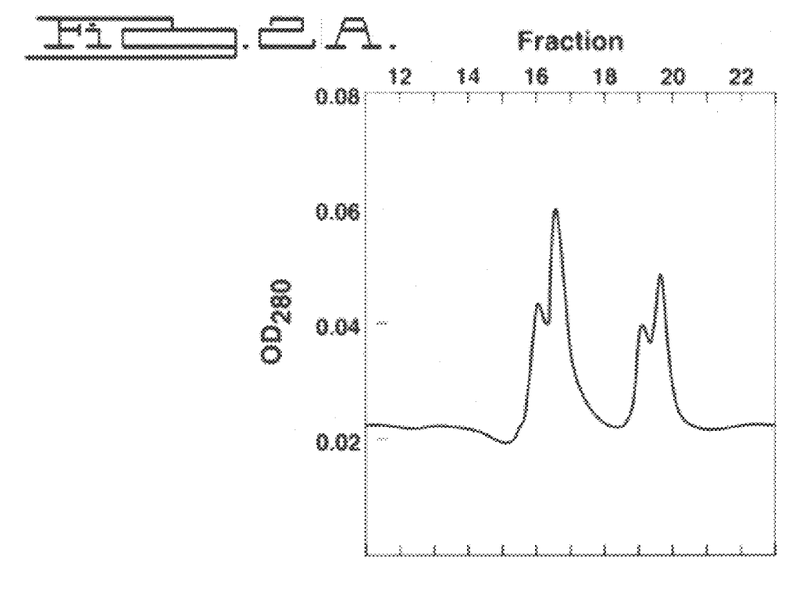
FIGS. 2A–2C show the final purification step of SafBP by anion exchange HPLC with FIG. 2A showing absorbance at 280 nm ($OD_{280}$), FIG. 2B showing SDS-PAGE of aliquots of each HPLC fraction, and FIG. 2C showing [$^3$H]Saf binding in each fraction.
Figure 2B:
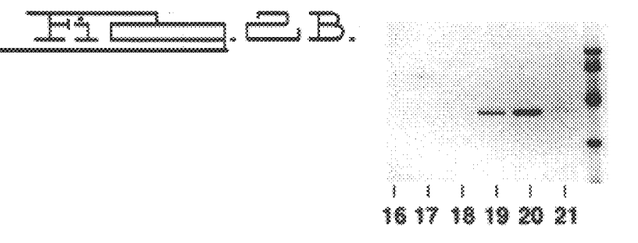
Figure 2C:
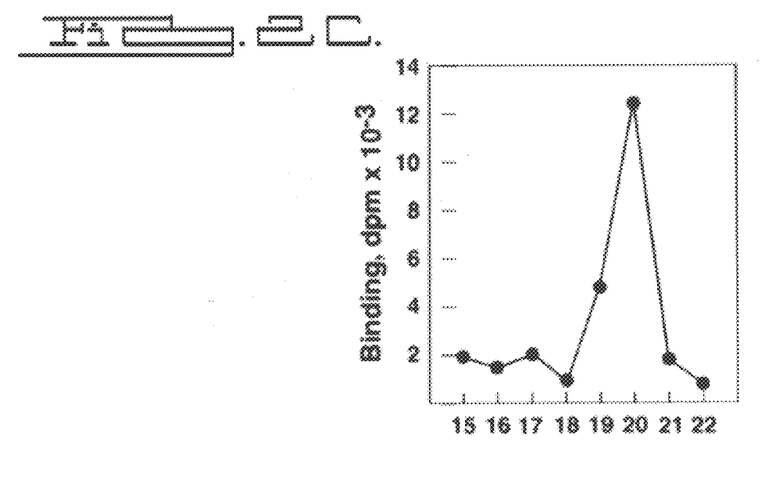

Purification of SafBP. The safener binding protein (SafBP) that accounts for safener binding activity (SafBA) (Walton, J. D. and Casida, J. E., *Plant Physiol.* 109:213–219 (1995)) was purified to electrophoretic homogeneity by ammonium sulfate precipitation and three chromatographic steps. FIGS. 2A–2C show the final purification step of SafBP by anion exchange HPLC; FIG. 2A shows $OD_{280}$, FIG. 2B shows the SDS-PAGE of aliquots of each HPLC fraction, and FIG. 2C shows [$^3$H]Saf binding. Equivalent HPLC fractions are aligned vertically in A, B, and C. SafBA was associated with the presence of a single protein of 39 kd, and at no step in the purification was there any evidence for additional SafBPs. By gel filtration, SafBP has a mass of 45 kd, and is therefore probably a monomer in its native state (data not shown). Based on Scatchard analysis showing that coleoptiles contain 55 pmol SafBA per mg protein (Walton, J. D. and Casida, J. E., *Plant Physiol.* 109:213–219 (1995)), and assuming that the binding stoichiometry is one, it is estimated that SafBP comprises 0.2% of the total protein in the coleoptile. [$^3$H]Saf binding to purified SafBP was competitively inhibited by thiocarbamate and chloroacetanilide herbicides (data not shown), as was SafBA in crude extracts. Walton, J. D. and Casida, J. E., *Plant Physiol.* 109:213–219 (1995).

Figure 3:
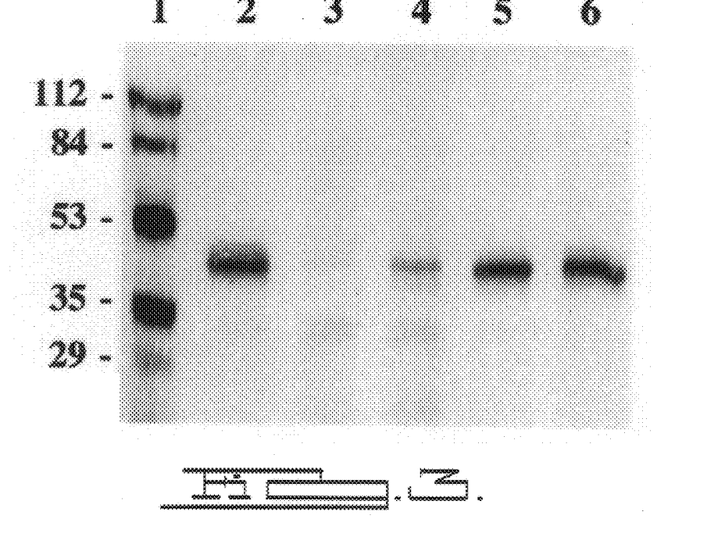
FIG. 3 is an immunoblot showing distribution of SafBP in etiolated maize seedlings.

Immunological Analysis of SafBP. FIG. 3 is an immunoblot showing distribution of SafBP in etiolated maize seedlings. Node extracts included approximately 0.3 mm of tissue on either side. Lane 1, molecular weight markers (sizes in kd); lane 2, coleoptile; lane 3, leaf; lane 4, node; lane 5, mesocotyl; lane 6, root. Each lane of an SDS-PAGE gel was loaded with 80 $\mu$g protein. After transfer to nitrocellulose, the blot was reacted with rabbit anti-SafBP antiserum and visualized with alkaline phosphatase coupled

TABLE I

Peptides obtained from purified SafBP

| Tryptic Peptide Sequence | Deduced Amino Acid Sequence Position in SBP1 |
|---|---|
| 1. AFADIWFV | 16- AqADIWrI |
| 2. DKQSSE(E)(G)(M)Y(L)ISPV(S)YL | 87- DKQSSEEerYrISPVSYL |
| 3. DVVTSPFEELXGAT(L) | 143- DVVTSPFEELhGATL |
| 4. DHLHGATLFHESMGSL | 150- eeLHGATLFHESMGSL |
| 5. DNFGIEIAMXEF | 181- DNFGIEIAMrEF |
| 6. DGAVKNYVEGRQ | 242- DGAmiNYVEGdm |
| 7. LLAELFT | 334- ewsELFT |
| 8. DLFTKAGFSEYKILKEFGA | 337- eLFTKAGFSEYKILKEFGA |

RNA Analysis. RNA was extracted from etiolated maize seedlings and tissues following freezing in liquid nitrogen by the method of de Vries et al., *Plant Mol. Biol. Man.* B6:1–13 (1988). Total RNA (30 $\mu$g per lane) was fractionated by agarose gel electrophoresis with formaldehyde and blotted to Nytran (Schleicher and Schuell) as described. Sambrook, J., et al., *Molecular Cloning: A Laboratory Manual*, 2nd ed., Cold Spring Harbor Laboratory, Cold Spring Harbor, N.Y. (1989). Hybridization was carried out by the method of Singh et al. (Singh, L. et al., *Nucl. Acids Res.* 12:5627–5638 (1984)) at 65° C. and the filters were washed twice for 10 and 60 min at 65° C. in 0.2× SSPE, 0.2% SDS prior to autoradiography. Size of the SBP1 mRNA was estimated using a 0.24 to 9.5-kb RNA ladder to goat anti-rabbit anti-IgG. SafBP is present in the coleoptile, mesocotyl, and root, and to a lesser extent, in the node and leaf, consistent with earlier results showing that SafBA is most abundant in the coleoptile, present in the node, mesocotyl, and roots, and scarcest in the leaf. Walton, J. D. and Casida, J. E., *Plant Physiol.* 109:213–219 (1995).

Figure 4:
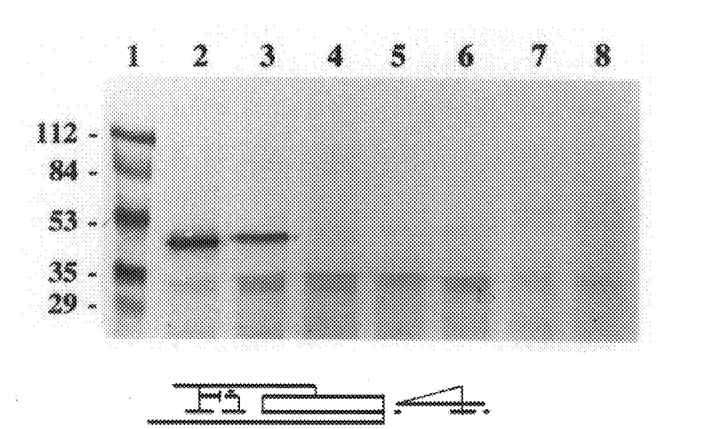
FIG. 4 shows immunoblot extracts of various etiolated plants.

FIG. 4 shows immunoblot of extracts of various etiolated plants. Blotting and visualization were done as described in FIG. 3 and Materials and Methods. Lane 1, molecular mass markers (sizes in kd); lane 2, maize; lane 3, sorghum; lane 4, wheat; lane 5, barley; lane 6, oats; lane 7, Arabidopsis; lane 8, tobacco. Each lane was loaded with 80 $\mu$g protein. Antiserum against purified SafBP recognizes a protein of 39 kd in maize and sorghum, both of which have SafBA, and not in wheat, oats, or barley, which do not have SafBA. Walton, J. D. and Casida, J. E., *Plant Physiol.* 109:213–219 (1995). Arabidopsis and tobacco, which also lack SafBA (unpublished data), also lack a protein recognized by anti-SafBP antiserum (FIG. 4).

Cloning of a CDNA Encoding SafBP. Based on peptides obtained from proteolytic digests of SafBP (Table I), three independent cDNAs encoding SafBP were isolated. All three cDNAs are approximately the same length and have the same or overlapping nucleotide sequence for at least 200 bp in from either end. One cDNA, SBP1, was sequenced in its entirety on both strands; the sequence of cDNA encoding SafBP and its deduced amino acid sequence are set forth in SEQ ID Nos. 1 and 2, respectively, and in FIG. 5. The two peptides used to design the PCR primers are indicated by underlining in FIG. 5. SBP1 has a single reading frame encoding a protein of 363 amino acids from the first in-frame methionine to the first stop codon. The predicted product is hydrophilic and has a mass of 40,252 and a pI of 5.93, consistent with the biochemical properties of SafBP.

Figure 6:
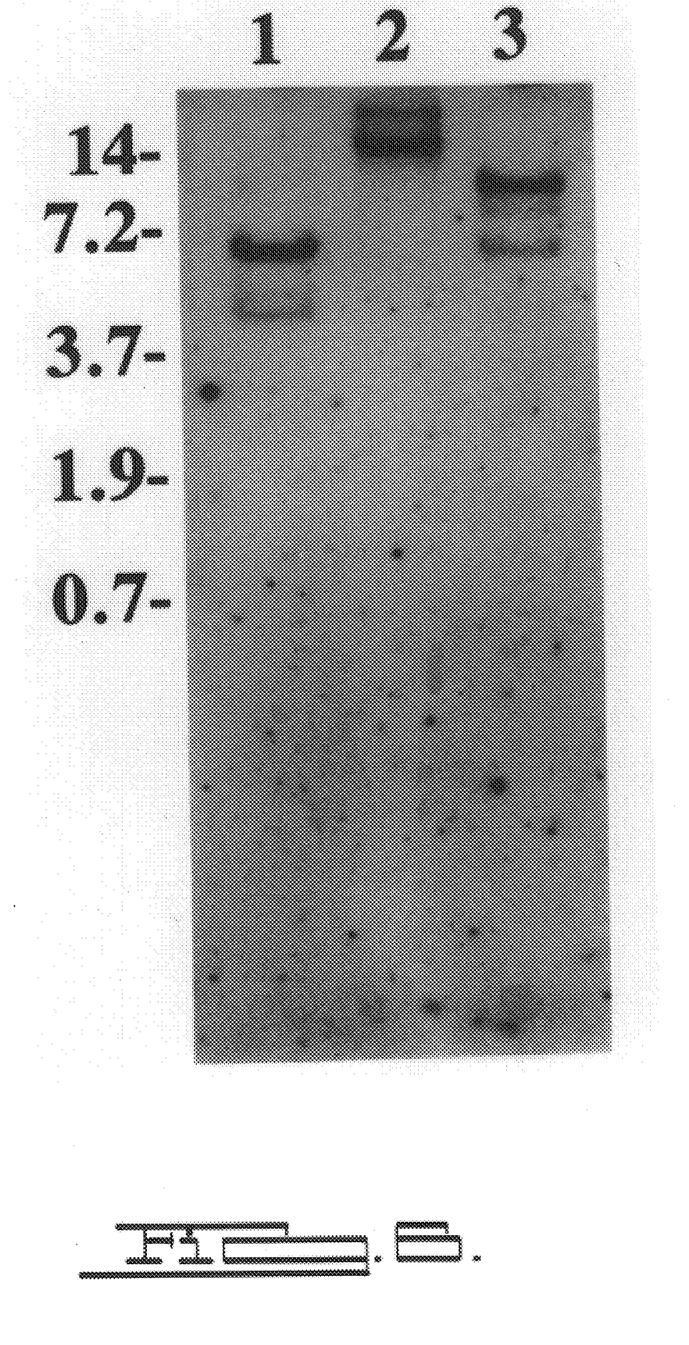
FIG. 6 is a Southern blot of maize DNA probed with SBP1 under high stringency conditions.
Figure 7:
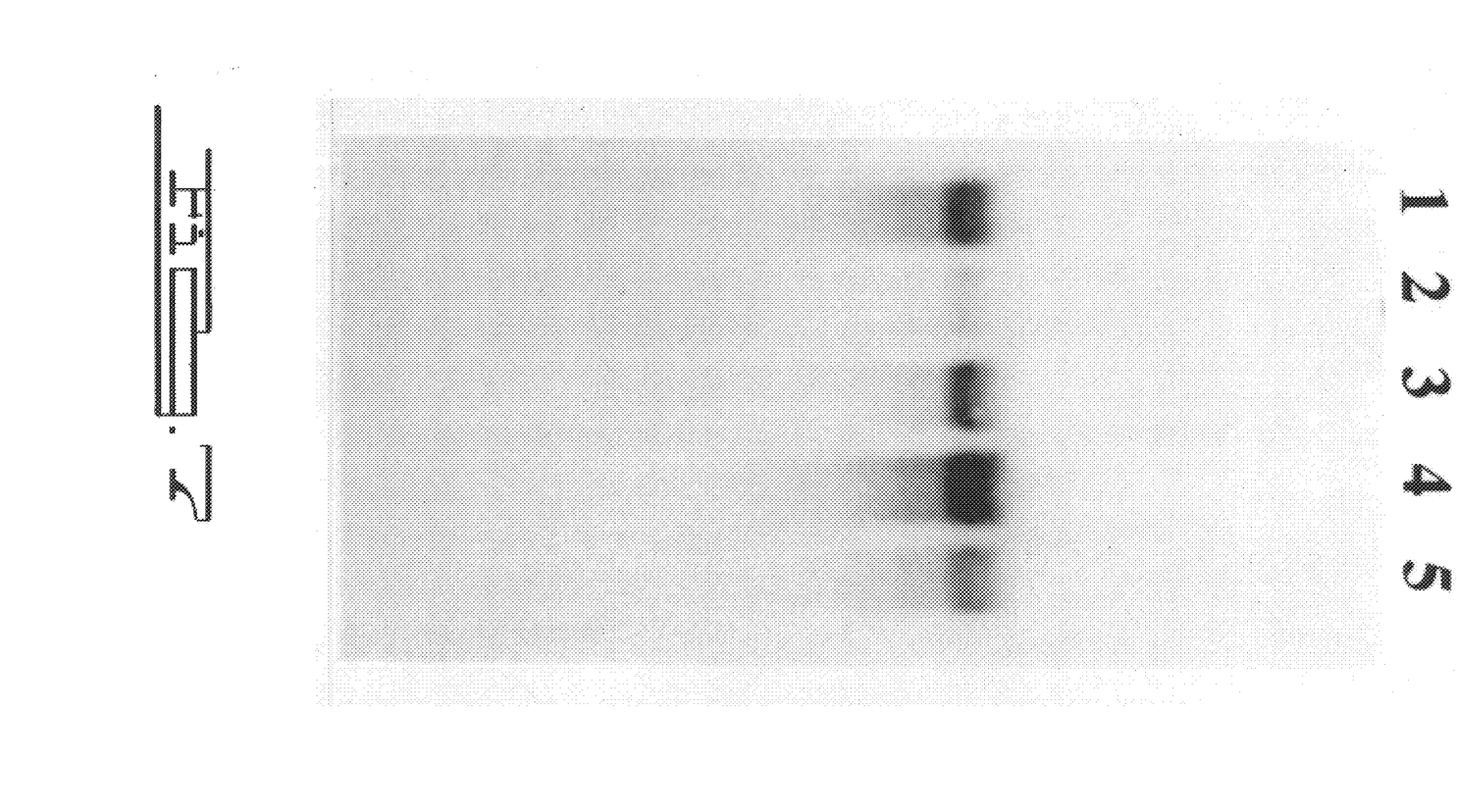
FIG. 7 is an RNA blot of different tissues of etiolated maize seedlings probed with SBP1.

On Southern blots that were probed and washed at high stringency, SBP1 hybridizes strongly with one major band and weakly to at least one other band, as shown in FIG. 6. DNA was cut with BamHI, EcoRI, or HindIII in lanes 1, 2, and 3, respectively. Markers are shown on the left in kb. SBP1 also hybridizes with sorghum DNA but, even at low stringency, SBP1 does not hybridize with DNA from oats, wheat, or barley (data not shown). FIG. 7 shows the RNA blot of different tissues of etiolated maize seedlings probed with SBP1. Equal loading in each lane was confirmed by staining of the rRNA bands with ethidium bromide. The SBP1 mRNA is approximately 1.5 kb. The RNA blotting indicated that the SBP1 mRNA is present in all parts of the etiolated maize seedling but is present only at low levels in the leaves.

Analysis of the sequence of SafBP. By TBLASTN (Atschul et al., *J. Mol. Biol.* 215:403–410 (1990)) and TFASTA (Program Manual for the Wisconsin Package, Genetics Computer Group, Madison, Wis. (1994)), SafBP is related to a number of known or putative O-methyltransferases (OMTs) that methylate phenolic compounds such as catechol, lignin precursors, and flavonoids. High BLAST scores were also obtained to OMTs involved in methylation of inositol, acetylserotonin, and hydroxyindole. Like SafBP, most of the similar plant OMTs are soluble proteins of approximately 40 kd. The amino acid sequence of SafBP is most closely related to a putative OMT in barley that is induced by pathogens and UV light, with an overall identity/similarity of 38%/63%. Gregerson, P. L., et al., *Plant Mol. Biol.* 26:1797–1806 (1994); GenBank X77467. In contrast to the barley OMT, however, SafBP is constitutively expressed and is not induced further by infection with the pathogen *Cochliobolus carbonum* (data not shown). The sequence of SafBP is also related to a putative OMT whose mRNA, ZRP4, is abundantly expressed in maize roots (34% identity, 60% similarity; Held et al., 1993; GenBank L14063) and that might be involved in the biosynthesis of suberin phenolics of the Casparian strip. Like SBP1, ZRP4 is poorly expressed in leaves. Held et al., *Plant Physiol.* 102:1001–1008 (1993). The closest match of SafBP to any protein of established function is to a maize caffeic acid O-methyltransferase (the product of the bm3 gene) with 30% identity and 54% similarity. Collazo P., et al., *Plant Physiol.* 20:857–867 (1992); Vignols, F., et al., *Plant Cell* 7:407–416 (1995); accession number M73235. SafBP is also related to a caffeic acid OMT from alfalfa (29% identity and 53% similarity; Gowri, G., et al., *Plant Physiol.* 97:7–14 (1991); accession number M63853). The sequence of SafBP shows no significant similarity to other classes of methyltransferases, including protein methylases, DNA methylases, and those that use CoA derivatives as substrates (e.g., Pakusch, A-E, et al., *Plant Physiol.* 96:327–330 (1991)).

Three conserved motifs have been found in most OMTs. Kagan, R. M., et al., *Arch. Biochem. Biophys.* 310:417–427 (1994). SafBP has a reasonable match to consensus motif II in the correct position [consensus: (G/P)(T/Q)(A/Y/F)DA (Y/V/I)(I/F)(L/V/C); SafBP: PPAQTVVL (SEQ ID NO:9) starting at amino acid 258; matches shown in bold type face] but does not have the highly conserved central aspartic acid residue. SafBP does not have a good consensus motif III in the proper position relative to motif II, but this motif is also not well conserved among known plant phenolic OMTs. In this region, the plant OMTs and SafBP share the sequence GKVI (starting at amino acid 295). Most significantly, however, SafBP lacks motif I, which is not only the most highly conserved of the motifs among all OMTs but is found in all of the plant phenolic OMTs.

Discussion

SafBP binds active compounds with high affinity and is abundant in the coleoptile, which is believed to be an important tissue for the action of safeners and herbicides. SafBP is present in maize and sorghum, which respond to safeners, and absent in wheat, oat, and barley, which do not respond. Immunoblotting established that the absence of SafBA in plants other than maize and sorghum is due to lack of SafBP. In addition, the species and tissue distribution of SafBP determined immunologically is consistent with the distribution based on SafBA. Walton, J. D. and Casida, J. E., *Plant Physiol.* 109:213–219 (1995). Intriguingly, SafBP also strongly binds the herbicides themselves in a competitive manner.

SPECIFIC EXAMPLE 2

Materials and Methods

Expression of SafBP in *E. coli*. Vector pZL1 (Gibco-BRL) containing the SafBP cDNA clone was digested with EcoRI and NotI, the 1.5-kb insert cloned into the corresponding sites in the *E. coli* expression vector pET21c (Novagen, Madison, Wis.), and the resulting construct transformed into *E. coli* strain BL21(DE3) (Novagen). A 50-mL culture of this strain was grown at 37° C. to an $OD_{600}$ of 0.5 at which point expression of the cDNA was induced with 1 mM isopropylthiogalactoside (IPTG). As a control, *E. coli* BL21 (DE3) transformed with pET21c with no insert was grown in parallel. Samples (each 12.5 mL) were removed at 0, 1, 2, and 3 hr after induction, centrifuged, and extracted by the freeze-thaw method according to Novagen, and centrifuged again to remove cell debris. Each sample was in a final volume of 5 mL of 50 mM Tris-HCl, pH 8; 50 μL of this was used in the [$^3$H]Saf binding assay according to Walton and Casida. Walton, J. D. and Casida, J. E., *Plant Physiol.* 109:213–219 (1995).

Discussion

SBP1 was expressed in *E. coil* behind an IPTG-inducible promoter. Extracts of *E. coil* expressing SBP1 have strong SafBA whereas cells transformed with the empty expression vector have no binding (Table II). Table II below shows [$^3$H]Saf binding in extracts of *E. coli* expressing SBP1. After growing to an $OD_{600}$ of 0.5, cells were induced with IPTG and aliquots harvested at the indicated times after induction, lysed, and centrifuged to remove cell debris. Final volume of each extract was 5 mL. Control cells were transformed with the vector without insert. Values are the average of duplicates. Like [$^3$H]Saf binding to the native maize protein, [$^3$H]Saf binding in *E. coli* extracts is inhibited by dichlormid, EPTC, metolachlor, acetochlor, and alachlor (Table III). Table III provides inhibition of [$^3$H]Saf binding by safeners and herbicides in extracts of *E. coli* expressing SBP1. The *E.coli*/SBP1 2-hr time point from Table I was used; protein content per sample was 20.9 µg. Values are the average of duplicates.

TABLE II

| | Control | | SBP1 | |
|---|---|---|---|---|
| Time (hr) | Protein[a] (µg) | Specific Binding[a] (dpm × 10$^{-3}$) | Protein[a] (µg) | Specific Binding[a] (dpm × 10$^{-3}$) |
| 0 | 3.8 | 0 | 6.6 | 0 |
| 1 | 10.1 | 0 | 17.1 | 17.9 |
| 2 | 9.5 | 0 | 20.9 | 51.1 |
| 3 | 13.3 | 0 | 12.3 | 24.6 |

[a]per 50 µL *E. coli* extract

TABLE III

| | Concentration | Total [$^3$H]Saf binding |
|---|---|---|
| none ([$^3$H]R-29148 alone) | | 67.3 |
| + R-29148 (120 nM) | 2.5 | 3.0 |
| + dichlormid (10 nM) | 1.4 | 0.7 |
| + EPTC (110 nM) | 1.6 | 1.7 |
| + acetochlor (180 nM) | 1.1 | 21.6 |
| + metolachlor (40 nM) | 1.1 | 3.3 |
| + alachlor (70 nM) | 1.1 | 1.7 |

[a]IC$_{50}$'s (in paraentheses) from Walton and Casida (Walton, J. D. and Casida, J. E., Plant Physiol. 109:213–219 (1995)).

SPECIFIC EXAMPLE 3

The SBP1 cDNA encoding SafBP was first subcloned as a PstI-NotI fragment into cloning vector pSP72 (Promega Corp.). The cDNA was released from pSP72 as a HindIII-BgIII fragment and cloned into the plant transformation vector pGA748 (An, G., Binary Ti plasmid vectors. *Methods Mol. Biol.* 44:47–58 (1995)) to create plasmid pHSBP1. This plasmid was used to transform cells of *Agrobacterium tumefaciens* strain LB4404 by electroporation using a Bio-Rad GenePulser with settings of 25 µF, 2.5 kV, 2000 ohms for 4 msec and transformants were selected on LB plates containing 12.5 µg/ml tetracycline and 50 µg/ml kanamycin.

Excised leaves from sterile tobacco plants (cultivar SR-1) were transformed to kanamycin resistance by the method of Newman et al. (*Plant Cell* 5:701–714 (1993)). Fifty independent transformants were regenerated and seed collected.

Figure 8:
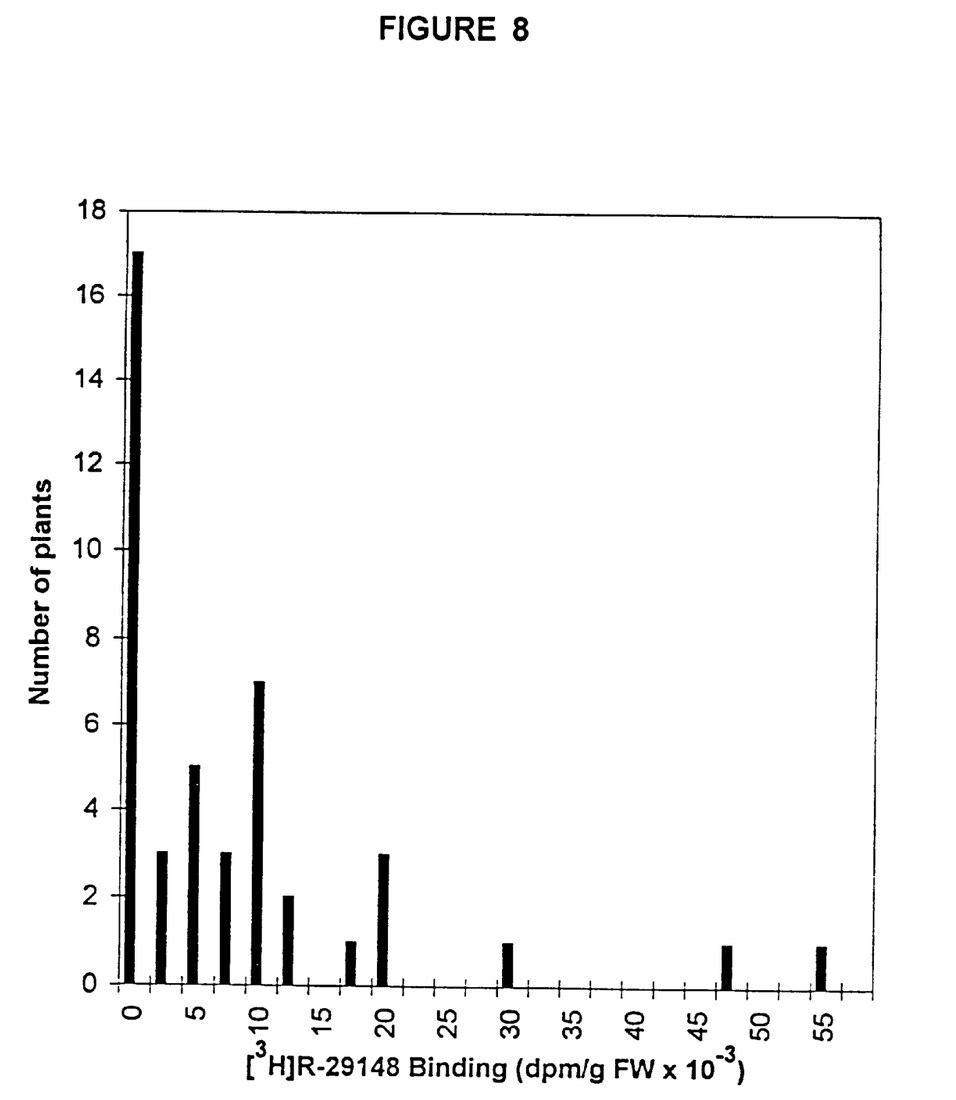
FIG. 8 is a graph showing [$^3$H]R-29148 binding in transgenic tobacco plants.
Figure 9:
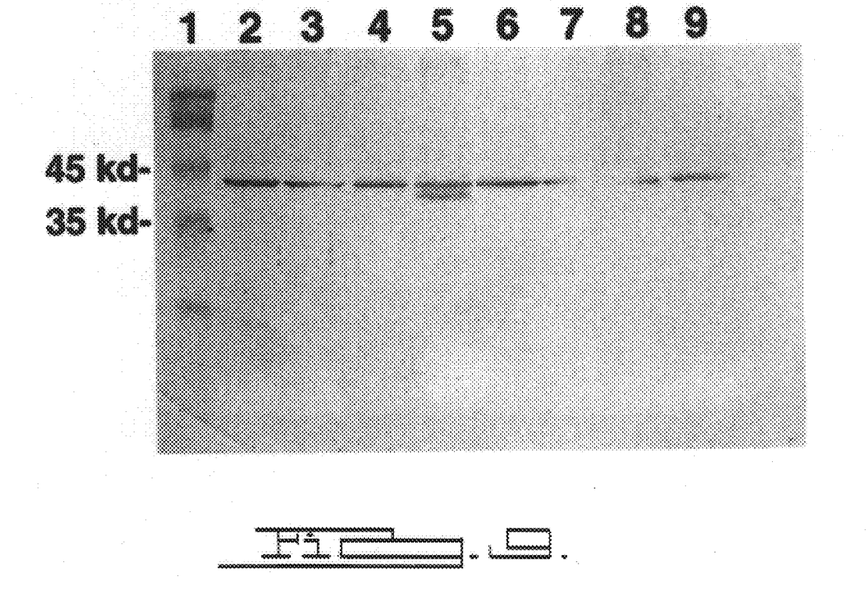
FIG. 9 is an immunoblot of SafBP in transgenic tobacco plants.

From 44 of the primary transformants, a piece of green leaf tissue (ca. 0.5 gm) was ground as described for corn (Walton, J. D. and Casida, J. E., *Plant Physiol.* 109:213–219 (1995)) and fractionated with ammonium sulfate. The fraction precipitating between 40% and 75% saturation was redissolved in 1 ml buffer (50 mM Tris, pH 8) and 50 µl of this used in the standard [$^3$H]R-29148 binding assay (Walton, J. D. and Casida, J. E., *Plant Physiol.* 109:213–219 (1995)). FIG. 8 shows binding results with 44 tobacco plants. Binding is shown on fresh weight (FW) basis. Binding in control (untransformed) tobacco plants was less than 600 dpm per gm fresh weight. Many transformed plants showed no safener binding activity, but twenty-four plants had significant binding (>5000 dpm per gm FW). As shown in FIG. 9, immunoblotting following SDS-PAGE of protein extracts of six transformed plants (T1 through T6) and a non-transformed control (C1, lanes 2 and 3) shows that the anti-SafBP antibody cross-reacts with a band of ca. 40 kDa in all green tobacco plants extracts. Lane 1: molecular weight standards, sizes in kilodaltons (kd). Lanes 2 and 3: extracts of two leaves from one control plant (untransformed); Lanes 3 through 9, extracts from six independent tobacco plants transformed with pHSBP1 containing an expressible cDNA SBP1. Binding in these plants was as follows (dpm [$^3$H]R-29148 binding per gm FW), average of duplicate assays. The binding assay background is approximately 500 dpm. Control 1 (lane 2): 542 dpm; Transformant (T) 1 (lane 4): 2024; T2 (lane 5): 9776; T3 (lane 6): 1327; T4 (lane 7): 1030; T5 (lane 8): 2541; and T6 (lane 9): 1195. One transformant plant (T3) shows a second band, of 39 kDa (lane 5, FIG. 9), and of the 7 plants shown in FIG. 9 this plant has the highest binding. The other plants show a low level of binding which is barely different from the wild type background binding. The low level of binding in these other plants (T1, T2, T4, T5, and T6) is correlated with inability to detect a new protein of 39 kd (SafBP) on immunoblots (FIG. 9).

The seed from the transformed plants was sown in soil and sprayed with Dual (metolachlor) or Dual II (metolachlor plus benoxacor (a dichloroacetamide safener—see Walton, J. D. and Casida, J. E., *Plant Physiol.* 109:213–219 (1995)) using a standard laboratory spray trial apparatus. The concentration was 1% in water, spray rate 152 ml per 30 sec, 12 inches above pots. This treatment killed control tobacco plants. Seed from transformants T1, T3, and T6 (low SafBA); T2 (moderate binding activity) and T15 (high binding activity) were tested. All were killed equally well by Dual or Dual II. Therefore, expression of SafBP does not apparently give any resistance to metolachlor nor does it confer detectable responsiveness to the dichloroacetamide safener benoxacor. However, this is not considered a definitive test for two reasons. First, tobacco is a dicot, and the protein of the present invention is from a monocot. Dicots and monocots are well known to differ considerably in their physiological response to herbicides and herbicide safeners, and tobacco might lack the necessary cellular transduction pathways to respond to safeners, even in the presence of SafBP. Second, metolachlor is not used on tobacco because in general it is not very effective against dicot plants such as tobacco. The study was performed in tobacco because tobacco is easy to transform. However, a better test of the utility of SafBP would be in wheat, oats, or barley. These plants could be transformed by those skilled in the art, with SBP1 using available technologies (e.g., H. Zhou et al., Plant Cell Reports 15:159–163 (1995); K. A. Torbert, H. W. Rines, and D. A. Somers, Plant Cell Reports 14:635–640 (1995); H. Funatsuki, H. Kuroda et al., *Theor. Appl. Gen.* 91:707–712 (1995)).

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

All patents and other publications referred to herein are expressly incorporated by reference.

What is claimed is:

1. An isolated and purified nucleic acid encoding plant SafBP, comprising a nucleotide sequence that hybridizes to SEQ ID NO: 1 or the complement of SEQ ID NO. 1 under high stringency wash conditions of 0.2× SSC at 65° C.

2. The isolated and purified nucleic acid of claim 1, wherein the nucleotide sequence encodes the polypeptide of SEQ ID NO: 2.

3. An expression vector comprising a nucleotide sequence encoding the polypeptide of SEQ ID NO: 2 operatively-linked to a promoter functional in a host cell.

4. The expression vector of claim 3, wherein the nucleotide sequence is that of SEQ ID NO 1.

5. A plant containing the expression vector of claim 3.

6. A method for increasing safener binding activity in a plant comprising the steps of introducing a nucleic acid comprising a nucleotide sequence encoding the polypeptide of SEQ ID NO: 2 into a plant cell and regenerating a plant from the plant cell.

7. The method of claim 6, wherein the nucleotide sequence is operatively-linked to a regulatory element which amplifies expression of the nucleic acid.

8. The method of claim 6, wherein the nucleic acid has the nucleotide sequence of SEQ ID NO: 1.

9. A transgenic plant produced by the method of claim 6.

10. A transgenic plant produced by breeding the plant of claim 9, wherein the plant retains the trait of increased safener binding activity.

11. The seeds of the plant of claim 9.

12. The seeds of the plant of claim 10.

13. A method for increasing thiocarbamate herbicide binding activity in a plant comprising the steps of introducing a nucleic acid comprising a nucleotide sequence encoding the polypeptide of SEQ ID NO: 2 into a plant cell and regenerating a plant from the plant cell.

14. The method of claim 13, wherein the nucleotide sequence is operatively-linked to a regulatory element which amplifies expression of the nucleic acid.

15. The method of claim 13, wherein the nucleic acid has the nucleotide sequence of SEQ ID NO: 1.

16. A transgenic plant produced by the method of claim 13.

17. A transgenic plant produced by breeding the plant of claim 16, wherein the plant retains the trait of increased thiocarbamate herbicide binding activity.

18. The seeds of the plant of claim 16.

19. The seeds of the plant of claim 17.

20. A method for increasing chloroacetanilide herbicide binding activity in a plant comprising the steps of introducing a nucleic acid comprising a nucleotide sequence encoding the polypeptide of SEQ ID NO: 2 into a plant cell and regenerating a plant from the plant cell.

21. The method of claim 20, wherein the nucleotide sequence is operatively-linked to a regulatory element which amplifies expression of the nucleic acid.

22. The method of claim 20, wherein the nucleic acid has the nucleotide sequence of SEQ ID NO: 1.

23. A transgenic plant produced by the method of claim 20.

24. A transgenic plant produced by breeding the plant of claim 23, wherein the plant retains the trait of increased chloroacetanilide herbicide binding activity.

25. The seeds of the plant of claim 23.

26. The seeds of the plant of claim 24.

* * * * *

SEQUENCE LISTING

<160> NUMBER OF SEQ ID NOS: 9

<210> SEQ ID NO 1
<211> LENGTH: 1438
<212> TYPE: DNA
<213> ORGANISM: Zea mays

<400> SEQUENCE: 1

| | | | | | |
|---|---|---|---|---|---|
| cacatacaca | agcacaagcg | cactctagca | atggcttctg | aggttgtccg | ccctagcgac | 60 |
| gccgagctac | taaaggcaca | agccgacata | tggcggctca | gcctctccta | cctcacgccc | 120 |
| ctgtcactga | ggtgcgccgt | ggagcttggc | atccctacgg | cgatctaccg | ccatggcggg | 180 |
| gctgcctcag | ccgctgagct | ggtcacgcg | ctgtctctcc | cctccactaa | gctgccgttc | 240 |
| ctccgccgcc | tgctgcggct | cctcgccgcg | tcgggcgtgt | tcaccgtcga | caagcagagc | 300 |
| tcggaggagg | agcggtaccg | catcagcccc | gtgtcctacc | tcctggtgga | cggcatccct | 360 |
| cacgaggacc | acatgaacca | caccgctctg | gtgctcacct | gcacctcgac | gcgctacatc | 420 |
| gaggcgggga | tagggctggc | ggagtggttc | aagaggacg | tggtcacgtc | accgttcgag | 480 |
| gagctgcacg | ggcgactct | gttccacgag | agcatgggga | gcctcgacgc | agatttccac | 540 |
| gacatggcga | gcgaggcctt | ggacgcccac | gacaacttcg | gcatcgagat | agctatgcgg | 600 |
| gagttcaggg | acttgttcga | ggggatccag | tccatgacct | actgctgcgg | taacttcggt | 660 |
| gatgacaagg | gtgccagggc | cattgtcaaa | gccttccac | acataaaatg | cactgtgctg | 720 |
| gcccctccca | agatcattgc | caccaaaccg | gccgatggag | cgatgataaa | ctatgtcgaa | 780 |
| ggtgacatgt | tcagtttcat | tccacctgct | caaactgtcg | tgctaaagct | tgtgctgcac | 840 |
| cacctgaccg | atgaggagtg | cgtcaagctc | ctggctcaat | gccggaaggc | gattccttca | 900 |
| cggaaggatg | gcgggaaagt | tataatcggt | gatattatga | ttgaccactc | tgggcctatg | 960 |
| ctggaaactc | acctcctgat | ggacatcggc | atgatgacca | tgacaaaagg | acggcagaga | 1020 |
| gatgaaaaag | aatggagcga | gctcttcacc | aaagcagggt | tcagcgaata | caagatcctg | 1080 |
| aaggaatttg | gagctcgtgt | tgccttcgaa | gtctatccgt | gagattgcac | ctggactata | 1140 |
| catatatatt | tacatacata | tatgtatgtg | tgtgggtgcc | ttgcgtggct | tggcgtgatg | 1200 |
| atgtcataaa | taagagggt | gggtgtgctt | gcggtattca | tggatggcca | tggatctgag | 1260 |
| cacatgacgt | tggatgcttt | cttaaggctc | tcgtggatct | tctatatttg | gaagaagctg | 1320 |
| taaaataata | tatcgccatc | tagtgttggc | gttggcttgt | atgtactttg | tacctgcttt | 1380 |
| gttattttgt | gtaatatcga | gtaacctaat | gtatacttgc | ttactactat | cactaccg | 1438 |

<210> SEQ ID NO 2
<211> LENGTH: 363
<212> TYPE: PRT
<213> ORGANISM: Zea mays

<400> SEQUENCE: 2

Met Ala Ser Glu Val Val Arg Pro Ser Asp Ala Glu Leu Leu Lys Ala
 1               5                  10                  15

Gln Ala Asp Ile Trp Arg Leu Ser Leu Ser Tyr Leu Thr Pro Leu Ser
                20                  25                  30

Leu Arg Cys Ala Val Glu Leu Gly Ile Pro Thr Ala Ile Tyr Arg His
            35                  40                  45

Gly Gly Ala Ala Ser Ala Ala Glu Leu Val Thr Ala Leu Ser Leu Pro
        50                  55                  60

Ser Thr Lys Leu Pro Phe Leu Arg Arg Leu Leu Arg Leu Leu Ala Ala
 65                  70                  75                  80

Ser Gly Val Phe Thr Val Asp Lys Gln Ser Ser Glu Glu Arg Tyr
             85                  90                  95

Arg Ile Ser Pro Val Ser Tyr Leu Leu Val Asp Gly Ile Pro His Glu
            100                 105                 110

Asp His Met Asn His Thr Ala Leu Val Leu Thr Cys Thr Ser Thr Arg
            115                 120                 125

Tyr Ile Glu Ala Gly Ile Gly Leu Ala Glu Trp Phe Lys Arg Asp Val
        130                 135                 140

Val Thr Ser Pro Phe Glu Leu His Gly Ala Thr Leu Phe His Glu
145                 150                 155                 160

Ser Met Gly Ser Leu Asp Ala Asp Phe His Asp Met Ala Ser Glu Ala
                165                 170                 175

Leu Asp Ala His Asp Asn Phe Gly Ile Glu Ile Ala Met Arg Glu Phe
            180                 185                 190

Arg Asp Leu Phe Glu Gly Ile Gln Ser Met Thr Tyr Cys Cys Gly Asn
        195                 200                 205

Phe Gly Asp Asp Lys Gly Ala Arg Ala Ile Val Lys Ala Phe Pro His
    210                 215                 220

Ile Lys Cys Thr Val Leu Ala Pro Pro Lys Ile Ile Ala Thr Lys Pro
225                 230                 235                 240

Ala Asp Gly Ala Met Ile Asn Tyr Val Glu Gly Asp Met Phe Ser Phe
                245                 250                 255

Ile Pro Pro Ala Gln Thr Val Val Leu Lys Leu Val Leu His His Leu
            260                 265                 270

Thr Asp Glu Glu Cys Val Lys Leu Leu Ala Gln Cys Arg Lys Ala Ile
        275                 280                 285

Pro Ser Arg Lys Asp Gly Gly Lys Val Ile Ile Gly Asp Ile Met Ile
    290                 295                 300

Asp His Ser Gly Pro Met Leu Glu Thr His Leu Leu Met Asp Ile Gly
305                 310                 315                 320

Met Met Thr Met Thr Lys Gly Arg Gln Arg Asp Glu Lys Glu Trp Ser
                325                 330                 335

Glu Leu Phe Thr Lys Ala Gly Phe Ser Glu Tyr Lys Ile Leu Lys Glu
            340                 345                 350

Phe Gly Ala Arg Val Ala Phe Glu Val Tyr Pro
        355                 360

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:degenerate
      primer
<220> FEATURE:
<221> NAME/KEY: misc_difference
<222> LOCATION: (12)
<223> OTHER INFORMATION: n is either a,c,g or t/u.

<400> SEQUENCE: 3
gayaayttyg gnathga                                                      17

<210> SEQ ID NO 4
<211> LENGTH: 6
<212> TYPE: PRT
<213> ORGANISM: Zea mays

-continued

```
<400> SEQUENCE: 4

Asp Asn Phe Gly Ile Glu
  1               5

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence:degenerate
      primer
<220> FEATURE:
<221> NAME/KEY: misc_difference
<222> LOCATION: (3)
<223> OTHER INFORMATION: n is either a,c,g or t/u
<220> FEATURE:
<221> NAME/KEY: misc_difference
<222> LOCATION: (15)
<223> OTHER INFORMATION: n is either a,c,g or t/u

<400> SEQUENCE: 5
gcnccraayt cyttna                                               16

<210> SEQ ID NO 6
<211> LENGTH: 6
<212> TYPE: PRT
<213> ORGANISM: Zea mays

<400> SEQUENCE: 6

Leu Lys Glu Phe Gly Ala
  1               5

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:degenerate
      primer
<220> FEATURE:
<221> NAME/KEY: misc_difference
<222> LOCATION: (15)
<223> OTHER INFORMATION: n is either a,c,g or t/u

<400> SEQUENCE: 7
gartayaara thctnaa                                              17

<210> SEQ ID NO 8
<211> LENGTH: 6
<212> TYPE: PRT
<213> ORGANISM: Zea mays

<400> SEQUENCE: 8

Glu Tyr Lys Ile Leu Lys
  1               5

<210> SEQ ID NO 9
<211> LENGTH: 8
<212> TYPE: PRT
<213> ORGANISM: Zea mays

<400> SEQUENCE: 9

Pro Pro Ala Gln Thr Val Val Leu
  1               5
```